(12) United States Patent
Temple (10) Patent No.: US 10,881,756 B2
(45) Date of Patent: Jan. 5, 2021

(54) METHODS AND EQUIPMENT FOR TREATMENT OF ODOROUS GAS STREAMS FROM INDUSTRIAL PLANTS

(71) Applicant: Stephen R. Temple, Santa Cruz, CA (US)

(72) Inventor: Stephen R. Temple, Santa Cruz, CA (US)

( * ) Notice: Subject to any disclaimer, the term of this patent is extended or adjusted under 35 U.S.C. 154(b) by 92 days.

(21) Appl. No.: 13/926,976

(22) Filed: Jun. 25, 2013

(65) Prior Publication Data

US 2014/0003995 A1    Jan. 2, 2014

Related U.S. Application Data (60) Provisional application No. 61/665,861, filed on Jun. 28, 2012.

(51) Int. Cl.
*A61L 9/14*    (2006.01)
*B01D 53/14*    (2006.01)

(52) U.S. Cl.
CPC .............. *A61L 9/145* (2013.01); *B01D 53/14* (2013.01); *A61L 2209/211* (2013.01); *B01D 2251/106* (2013.01)

(58) Field of Classification Search
CPC ....................................................... A61L 9/145
USPC ........................................................... 422/4
See application file for complete search history.

(56) References Cited

U.S. PATENT DOCUMENTS

| | | |
|---|---|---|
| 1,969,021 A | 8/1934 | Nils |
| 3,021,189 A | 2/1962 | Mancke et al. |
| 3,342,545 A | 9/1967 | Jaeger |
| 3,572,010 A | 3/1971 | Dupps |
| 3,676,318 A | 7/1972 | Lauer |
| 3,717,701 A | 2/1973 | Carlson |
| 3,729,298 A | 4/1973 | Anderson |
| 3,883,329 A | 5/1975 | Dupps, Sr. |
| 3,905,774 A | 9/1975 | Kolting |
| 3,949,055 A | 4/1976 | Schneider et al. |
| 3,949,056 A | 4/1976 | Nakshbendi |
| 3,969,479 A | 7/1976 | Lonnes et al. |

(Continued)

FOREIGN PATENT DOCUMENTS

| | | |
|---|---|---|
| DE | 37 12 209 A1 | 10/1988 |
| DE | 19753117 A1 | 6/1998 |

(Continued)

OTHER PUBLICATIONS

U.S. Appl. No. 14/160,138, Temple.

(Continued)

*Primary Examiner* — Holly Kipouros
(74) *Attorney, Agent, or Firm* — Owens Law Firm, PC (57) ABSTRACT

The present invention is directed to a gas scrubbing process for removing at least one odorous vaporous compound from a gas stream generated by a rendering process or at least reducing the concentration of that odorous vaporous compound. In one embodiment, a series of two gas/liquid contactors is used, each having a different liquid scrubbing solution, with one scrubbing solution controlled at an alkaline pH and the other scrubbing solution controlled at an acidic pH. In another embodiment, the pH of the respective scrubbing solutions in each of the two gas/liquid contactors is reversed.

18 Claims, 2 Drawing Sheets

(56) References Cited

U.S. PATENT DOCUMENTS

| | | | |
|---|---|---|---|
| 3,985,820 A | 10/1976 | Albright | |
| 3,989,465 A | 11/1976 | Onnen | |
| 4,002,722 A | 1/1977 | Suzuki et al. | |
| 4,003,798 A | 1/1977 | McCord | |
| 4,092,446 A | 5/1978 | Padovani | |
| 4,172,880 A | 10/1979 | Tzavos | |
| 4,203,765 A | 5/1980 | Claeys et al. | |
| 4,265,088 A | 5/1981 | Funk | |
| 4,283,211 A | 8/1981 | Ehrlich | |
| 4,307,067 A | 12/1981 | Tagawa et al. | |
| 4,363,215 A | 12/1982 | Sharp | |
| 4,443,342 A | 4/1984 | Stas et al. | |
| 4,451,442 A | 5/1984 | Jeffrey et al. | |
| 4,455,287 A | 6/1984 | Primack | |
| 4,460,552 A | 7/1984 | Zakrzewski | |
| 4,595,577 A | 6/1986 | Stas et al. | |
| 4,614,646 A | 9/1986 | Christiansen | |
| 4,662,899 A | 5/1987 | Tandon | |
| 4,964,885 A | 10/1990 | Wieser-Linhart | |
| 5,019,339 A | 5/1991 | Keeney et al. | |
| 5,279,646 A | 1/1994 | Schwab | |
| 5,308,589 A | 5/1994 | Yung | |
| 5,567,402 A | 10/1996 | Vicard et al. | |
| 5,597,539 A | 1/1997 | Fakley et al. | |
| 5,945,078 A | 8/1999 | Taylor et al. | |
| 5,972,401 A | 10/1999 | Kowalski | |
| 6,015,536 A | 1/2000 | Lokkesmoe et al. | |
| 6,160,194 A | 12/2000 | Pignatello | |
| 6,183,708 B1 | 2/2001 | Hei et al. | |
| 6,190,629 B1 | 2/2001 | Solomon | |
| 6,375,721 B1* | 4/2002 | Holter | 96/66 |
| 6,459,011 B1 | 10/2002 | Tarr et al. | |
| 6,645,450 B2 | 11/2003 | Stoltz et al. | |
| 6,821,382 B1 | 11/2004 | Lundgren | |
| 6,843,835 B2 | 1/2005 | Fornai | |
| 6,926,878 B2 | 8/2005 | Santina | |
| 6,960,330 B1 | 11/2005 | Cox | |
| 7,112,309 B2 | 9/2006 | Stoltz | |
| 7,264,694 B2 | 9/2007 | Merrell | |
| 7,550,123 B2 | 6/2009 | Temple et al. | |
| 7,582,271 B2 | 9/2009 | Parrish et al. | |
| 7,815,879 B2 | 10/2010 | Temple | |
| 8,025,860 B1 | 9/2011 | Diamond | |
| 8,100,990 B2 | 1/2012 | Ellens | |
| 8,137,444 B2 | 3/2012 | Farsad | |
| 8,282,901 B2 | 10/2012 | Petrocelli | |
| 8,753,566 B1 | 6/2014 | Temple | |
| 8,795,475 B2 | 8/2014 | Hutchins | |
| 9,603,963 B2 | 3/2017 | Temple | |
| 2002/0034468 A1* | 3/2002 | Spink | B01D 53/48 423/220 |
| 2007/0059229 A1* | 3/2007 | Temple | A61L 9/145 423/243.01 |
| 2008/0152567 A1 | 6/2008 | Kilough | |
| 2008/0221314 A1 | 9/2008 | Freire | |
| 2009/0104099 A1 | 4/2009 | Au-Yeung | |
| 2010/0183738 A1 | 7/2010 | Kramer | |
| 2010/0280135 A1 | 11/2010 | Doty | |
| 2011/0061528 A1 | 3/2011 | Taylor | |
| 2011/0104012 A1 | 5/2011 | Temple | |
| 2011/0189049 A1* | 8/2011 | Beaulieu et al. | 422/5 |
| 2011/0258914 A1 | 10/2011 | Banasiak | |
| 2011/0280762 A1 | 11/2011 | Mattelmaki et al. | |
| 2012/0076716 A1 | 3/2012 | Suchak et al. | |
| 2012/0087827 A1 | 4/2012 | Temple | |
| 2012/0288570 A1* | 11/2012 | Zhu | D06L 3/021 424/616 |
| 2012/0304540 A1 | 12/2012 | Hulteberg | |
| 2017/0173204 A1 | 6/2017 | Temple | |

FOREIGN PATENT DOCUMENTS

| | | |
|---|---|---|
| DE | 19824903 C1 | 2/2000 |
| JP | 01317528 | 12/1989 |
| JP | 09094431 | 4/1997 |
| KR | 101 187 291 B1 | 10/2012 |
| WO | WO 81/03034 | 10/1981 |

OTHER PUBLICATIONS

U.S. Appl. No. 14/660,923, Temple.
U.S. Appl. No. 13/797,882, Temple.
Zahn et al., "Effect of a Packed-Bed Scrubber Using Radox Catalyst on the Emission of Odors and Volatile Organic Compounds from a Commercial Poultry Rendering Plant," Apr. 2002.
Sun et al., "Chemical Treatment of Pesticide Wastes—Evaluation of Fe(III) Chelates for Catalytic Hydrogen Peroxide Oxidation of 2,4-D at Circumneutral pH," J. Agric. Food Chem. vol. 40, pp. 322-327 (1992).
"Fenton's Reagent Iron Catalyzed Hydrogen Peroxide," http://www.h2o2.com/applications/Industrialwastewater/fentonsreagent.html (1996).
Rempp et al., "Polymer Synthesis," 2d rev. ed., Huthig & Wepf Verlag Basel, New York, p. 56 (1991).
"Use of Hydrogen Peroxide in Gas Scrubbing," Effluent and Water Treatment J., vol. 19, pp. 20-22 (1979).
"Storage and Handling of Hydrogen Peroxide," Effluent and Water Treatment J., vol. 19, pp. 34-37 (1979).
"Analysis of Aqueous Effluents," Effluent and Water treatment J., vol. 19, pp. 29-33 (1979).
"Advantages of Peroxygen Products in Pollution Control," Effluent and Water Treatment J., vol. 19, pp. 4-5 (1979).
"Catalytic Oxidation of Phenol with Hydrogen Pyeroxide," report from Interox Chemicals Ltd., Aug. 1978.
EP Search Report, dated Sep. 15, 2016.
Copending U.S. Appl. No. 14/274,682, Temple.

* cited by examiner

METHODS AND EQUIPMENT FOR TREATMENT OF ODOROUS GAS STREAMS FROM INDUSTRIAL PLANTS

CROSS-REFERENCES TO RELATED APPLICATIONS

This application claims the benefit of U.S. Provisional Application No. 61/665,861 filed Jun. 28, 2012. The foregoing application is hereby incorporated by reference herein in its entirety.

BACKGROUND

1. Background of the Invention

The invention and its various embodiments relate to methods and equipment for treating odorous gas streams and liquid waste streams from industrial plants, such as meat rendering plants and pet food manufacturing plants, as well as other industrial plants. More specifically, the invention and its various embodiments relate to the removal of odorous vaporous components from gas streams using a dual or two stage scrubbing process.

2. Description of Related Art

Control of odors is one of the most challenging problems faced by the animal byproduct processing industry, referred to as "rendering." In most facilities animal byproduct is brought into a processing facility and processed, in some cases, into animal feed. This process basically converts the byproduct, which consists of waste animal tissue and bone, into a stable value-added material such as purified animal fats (lard, tallow, and grease) and protein meals (meat, bone meal, and blood meal). However, operation of this process results in the production of odorous vapors.

More specifically, the rendering process is performed by "cooking" the animal byproduct to evaporate moisture and to separate fat from bone and protein. The resulting material is then processed to separate liquid fat from the solids. The solids are further processed to remove additional moisture (e.g., by using a screw press) and to generate a press cake that is made into a meal product. The liquid fat is also further processed to remove additional solids (e.g., by using a centrifuge) and then made into fat-based products.

However, in the process of cooking the animal byproduct, heat is added to the material resulting in the generation of vapors. These vapors carry odorous compounds such as hydrogen sulfide, ammonia, and volatile organic compounds (VOCs). In addition, other odorous vapors can be generated at other points in the rendering process. For example, odorous vapors can be generated from the screw press used to remove moisture from the solids produced in the cooking process to separate fat from protein solids or from the centrifuge used to remove solids from the liquid fat.

In most facilities an air scrubbing process is used to reduce or remove some of these odorous vapors. In this case, the various odorous vapors are passed as a gas stream to the air scrubbing process in which at least some of the odorous vaporous compounds are absorbed into a scrubbing solution, and the gas stream exiting the air scrubbing process is released into the atmosphere. However, such scrubbing processes do not remove all of the odorous compounds in the gas stream and a need exists to improve upon the performance of such air scrubbing processes.

SUMMARY OF THE INVENTION

In general, the present invention is directed to a process for removing at least one odorous vaporous compound from a gas stream or at least reducing the concentration of that odorous vaporous compound. In particular, the present invention is directed to a gas scrubbing process for removing at least one odorous vaporous compound from a gas stream generated by a rendering process or at least reducing the concentration of that odorous vaporous compound.

In one embodiment, the present invention provides a method for reducing the concentration of at least one odorous compound in a gas stream from a rendering process, comprising: passing a gas stream comprising at least one odorous compound through a first gas/liquid contactor; contacting the gas stream in the first gas/liquid contactor with a first liquid scrubbing solution; passing the gas stream from the first gas/liquid contactor through a second gas/liquid contactor; and contacting the gas stream in the second gas/liquid contactor with a second liquid scrubbing solution, wherein the first liquid scrubbing solution comprises an alkaline liquid scrubbing solution and the second liquid scrubbing solution comprises an acidic liquid scrubbing solution or wherein the first liquid scrubbing solution comprises an acidic liquid scrubbing solution and the second liquid scrubbing solution comprises an alkaline liquid scrubbing solution.

In another embodiment, the present invention provides a method for reducing the concentration of at least one odorous compound in a gas stream from a rendering process, comprising: passing a gas stream comprising at least one odorous compound through a first gas/liquid contactor; contacting the gas stream in the first gas/liquid contactor with a first liquid scrubbing solution; passing the gas stream from the first gas/liquid contactor through a second gas/liquid contactor; and contacting the gas stream in the second gas/liquid contactor with a second liquid scrubbing solution, wherein the first liquid scrubbing solution comprises an alkaline liquid scrubbing solution comprising hydrogen peroxide and the second liquid scrubbing solution comprises an acidic liquid scrubbing solution comprising a reaction product of hydrogen peroxide and a hydrogen peroxide decomposition additive, or wherein the first liquid scrubbing solution comprises an acidic liquid scrubbing solution comprising a reaction product of hydrogen peroxide and a hydrogen peroxide decomposition additive and the second liquid scrubbing solution comprises an alkaline liquid scrubbing solution comprising hydrogen peroxide.

Either of the foregoing embodiments may further include switching the operating pH of the scrubbing solution in each of the two gas/liquid contactors. In one embodiment, the first gas/liquid contactor utilizes a scrubbing solution controlled at an alkaline pH and the second gas/liquid contactor utilizes a scrubbing solution controlled at an acidic pH for a first period of time, after which the first gas/liquid contactor utilizes a scrubbing solution controlled at an acidic pH and the second gas/liquid contactor utilizes a scrubbing solution controlled at an alkaline pH for a second period of time, after which the first and second gas/liquid contactors utilize scrubbing solutions controlled at an alkaline and an acidic pH, respectively. In another embodiment, the first gas/liquid contactor utilizes a scrubbing solution controlled at an acidic pH and the second gas/liquid contactor utilizes a scrubbing solution controlled at an alkaline pH for a first period of time, after which the first gas/liquid contactor utilizes a scrubbing solution controlled at an alkaline pH and the second gas/liquid contactor utilizes a scrubbing solution controlled at an acidic pH for a second period of time, after which the first and second gas/liquid contactors utilize scrubbing solutions controlled at an acidic and an alkaline pH, respectively. The composition of the scrubbing solutions with respect to hydrogen peroxide and a hydrogen peroxide decomposition additive may be reversed as well.

DETAILED DESCRIPTION OF THE INVENTION

The present invention is more fully described below with reference to the accompanying drawings. While the invention will be described in conjunction with particular embodiments, it should be understood that the invention can be applied to a wide variety of applications, and it is intended to cover alternatives, modifications, and equivalents within the spirit and scope of the invention. Accordingly, the following description is exemplary in that several embodiments are described (e.g., by use of the terms "preferably," "for example," or "in one embodiment"), but this description should not be viewed as limiting or as setting forth the only embodiments of the invention, as the invention encompasses other embodiments not specifically recited in this description. Further, the use of the terms "invention," "present invention," "embodiment," and similar terms throughout this description are used broadly and are not intended to mean that the invention requires, or is limited to, any particular aspect being described or that such description is the only manner in which the invention may be made or used.

In general, the present invention is directed to a process for removing, or at least reducing the concentration of, at least one odorous vaporous compound from a gas stream. In particular, the present invention is directed to a gas scrubbing process for removing, or at least reducing the concentration of, at least one odorous vaporous compound from a gas stream generated by a rendering process.

In one embodiment, a series of two gas/liquid contactors is used, each having a different liquid scrubbing solution. In this case, a gas stream, such as a gas stream from a rendering process, containing one or more odorous vaporous compounds is passed through a first gas/liquid contactor. A scrubbing solution is used to absorb at least a portion of one or more odorous vaporous compounds from the gas stream. The gas stream then exits the first gas/liquid contactor and is passed to a second gas/liquid contactor. A different scrubbing solution is then used to absorb at least a portion of one or more odorous vaporous compounds from the gas stream, which may include some of the same odorous vaporous compounds absorbed in the first gas/liquid contactor or different odorous vaporous compounds. The gas stream is then discharged, for example, to the atmosphere.

In one embodiment, the scrubbing solution used in the first gas/liquid contactor is an alkaline scrubbing solution. In some embodiments, the pH of this scrubbing solution is greater than 7.0, 7.5, 8.0, 8.5, 9.0, 9.2, or 9.5 or higher. In some embodiments, this scrubbing solution includes hydrogen peroxide. In some embodiments, this scrubbing solution includes hydrogen peroxide and a hydrogen peroxide decomposition additive that catalyzes the decomposition of the hydrogen peroxide to enhance the effectiveness of the scrubbing solution to absorb the odorous vaporous compounds. In this case, the scrubbing solution will contain the reaction product or products or the decomposition of the hydrogen peroxide.

In one embodiment, the scrubbing solution used in the second gas/liquid contactor is an acidic scrubbing solution. In some embodiments, the pH of this scrubbing solution is less than 7.0, 6.5, 6.0, 5.5, or 5.0 or lower. In some embodiments, this scrubbing solution includes hydrogen peroxide. In some embodiments, this scrubbing solution includes hydrogen peroxide and a hydrogen peroxide decomposition additive that catalyzes the decomposition of the hydrogen peroxide to enhance the effectiveness of the scrubbing solution to absorb the odorous vaporous compounds. In this case, the scrubbing solution will contain the reaction product or products or the decomposition of the hydrogen peroxide.

The hydrogen peroxide decomposition additive may include any chemical that catalyzes the decomposition of hydrogen peroxide. For example, chemical elements selected from groups 3B, 4B, 5B, 6B, 7B, 8B, 1B, and 2B of the Periodic Table of Elements, such as fluorine; "d" block transition elements, such as cobalt; a source of ferrous or ferric ion, such as ferrous sulfate or ferric sulfate; or ozone may be used as hydrogen peroxide decomposition additives, alone or in combination. Such hydrogen peroxide decomposition additives and their use in rendering processes are described in U.S. Pat. No. 7,550,123, entitled "Method and Apparatus for Use of Reacted Hydrogen Peroxide Compounds in Industrial Process Waters," which is incorporated by reference herein in its entirety.

It should be appreciate that by using two scrubbers each with scrubbing solutions at different pHs, such an alkaline scrubbing solution or a scrubbing solution with a pH greater than 7.0 and an acidic scrubbing solution or a scrubbing solution with a pH less than 7.0, more odorous vaporous compounds may be absorbed since not all such compounds can be absorbed at the same pH, such as in a single scrubbing using a single scrubbing solution at a single pH. Moreover, it should be appreciated that the scrubbing solutions used in the two different gas/liquid contactors may be periodically switched. For example, an alkaline scrubbing solution used in a first gas/liquid contactor may be used in the second or downstream gas/liquid contactor and the acidic scrubbing solution used in a second gas/liquid contactor may be used in the first or upstream gas/liquid contactor. This be done, for example, to dissolve or remove any scale buildup using the acidic scrubbing solution that has occurred in the first gas/liquid contactor during operation with the alkaline scrubbing solution and vice versa. Accordingly, operation of both gas/liquid contractors to remove odorous vaporous components from a gas stream can be continued or maintained while concurrently cleaning the inside of the scrubber, for example, by removing scale buildup. After such scale buildup has been sufficiently removed, the scrubbing solutions can be reversed again and used as initially operated in their respective gas/liquid contactors.

It should be appreciated that other components can be added to either the acidic scrubbing solution or the alkaline scrubbing solution or both. For example, a chelating agent can be added in those embodiments in which a hydrogen peroxide decomposition additive is used to increase the solubility of this additive. Further still, other components such as a nonionic wetting agent or a low molecular weight dispersant polymer may be added to either scrubbing solution. Such other additives and their use in rendering processes are also described in U.S. Pat. No. 7,550,123, entitled "Method and Apparatus for Use of Reacted Hydrogen Peroxide Compounds in Industrial Process Waters."

Figure 1:
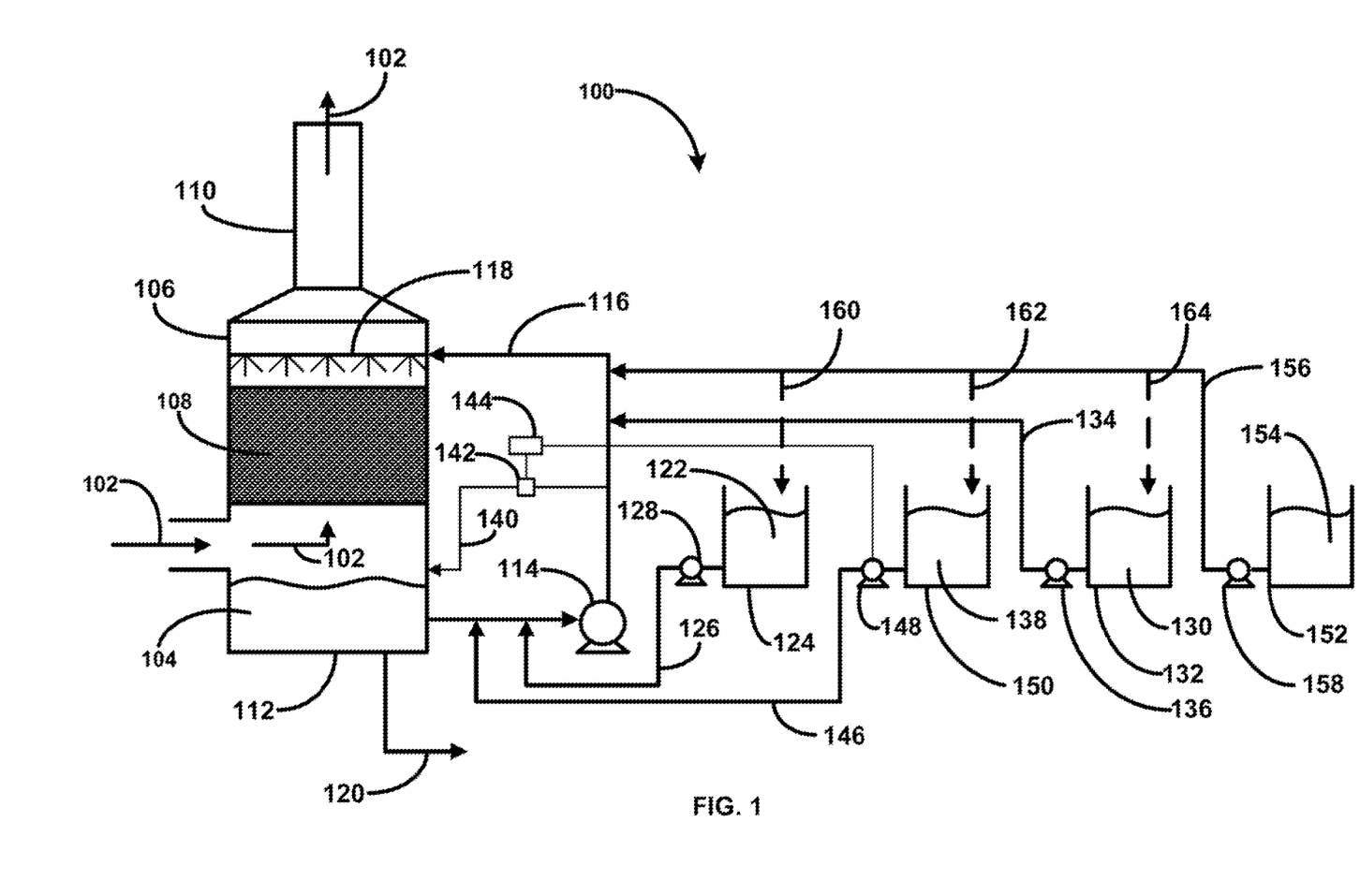
FIG. 1 is a flow diagram illustrating one of the two gas/liquid scrubbing systems according to one embodiment of the present invention.

FIG. 1 is a flow diagram illustrating one of the two gas/liquid scrubbing systems according to one embodiment of the present invention. In this embodiment, a wet scrubber system 100 is used to contact a gas stream 102 comprising an odorous vaporous compound with a scrubbing solution 104 comprising an aqueous solution of hydrogen peroxide and, optionally, at least one additive that catalyzes the decomposition of the hydrogen peroxide to remove the odorous vaporous compound from the gas stream 102 or to at least reduce the concentration of the odorous vaporous compound in the gas stream 102. If should be appreciated that this wet scrubbing system 100 may be used to remove more than one odorous vaporous compound from the gas stream 102.

In this embodiment, the gas stream 102 (as represented by the arrows) comprising at least one or more odorous vaporous compound enters a wet scrubber 106. The gas stream 102 may be from a food processing process, rendering process, or other industrial process that produces gaseous odoriferous and/or noxious components that have been collected. In this embodiment, the wet scrubber 106 comprises packing 108, although it should be appreciated that any type of gas/liquid contactor other than a packed bed may be used, including a spray tower with or without packing or a spray venturi. The gas stream 102 enters the wet scrubber 106 and passes through the packing 108 and through a stack or outlet duct 110 where the gas stream 102 is discharged to the atmosphere.

The wet scrubber 106 comprises a sump 112 that holds the scrubbing solution 104. In some embodiments, the sump 112 is integral to the scrubber 106; however, the sump 112 may also be separate from the scrubber 106. The scrubbing solution 104 is pumped by a pump 114 from the sump 112 through a recycle line 116 to a bank of spray nozzles 118 where is it discharged onto the packing 108. It should be appreciated that a wide variety of pumps may be used. The pump should be chosen to provide sufficient power to move fluid at the mass flow rate required by the particular scrubber relative to the gas flow rate and the concentration of the various vaporous compounds to be removed. It should also resist chemical attach by the scrubbing solution 104 and any additives present in the scrubbing solution 104. For certain applications, it may be desirable to use specific types of pumps. For example, when using the pump to introduce ozone or other gaseous hydrogen peroxide decomposition additives or catalysts as described further below, a pump capable of introducing a gas into a liquid stream could be used, such as a regenerative turbine pump. It should also be appreciated that the scrubbing solution 104 can be discharged onto the packing in any manner known in the art.

Once discharged onto the packing 108, the scrubbing solution 104 flows in a counter-current fashion to the direction of the gas stream 102. The packing 108 acts to facilitate contact between the gas stream 102 and the scrubbing solution 104 to allow for the absorption of one or more odorous vaporous compounds from the gas stream 102 into the scrubbing solution 104. Accordingly, the gas stream 102 that exits through the stack or outlet duct 110 has a reduced concentration of the odorous vaporous compounds.

After passing through the packing 108, the scrubbing solution 104 is collected in the sump 112 and recycled back to the top of the packing 108 through a recycle line 116. The sump 112 also has a discharge line 120 that allows either the entire scrubbing solution 104, or a portion thereof, to be discharged, for example, to a wastewater treatment system (not shown). One of skill in the art will appreciate that water may be added to the sump 112 depending upon the amount of scrubbing solution 104 discharged to maintain the water balance in the process and to maintain a desired level in the sump 112.

The scrubbing solution 104 comprises hydrogen peroxide and, optionally, at least one additive that catalyzes the decomposition of at least a portion of the hydrogen peroxide to hydroxyl radicals. In one embodiment, the additive that catalyzes the decomposition of hydrogen peroxide is used to produce hydroxyl free radicals such that the scrubbing solution 104 has a relatively high concentration of hydroxyl radicals upon discharge from the spray nozzles 118 compared to a hydrogen peroxide solution without a hydrogen peroxide decomposition additive.

In the scrubber 106, and particularly in the packing 108, the gas stream 102 and the scrubbing solution 104 comprising hydroxyl free radicals contact each other. During this contact, one or more odorous vaporous compounds in the gas stream 102 are absorbed by the scrubbing solution 104 and are oxidized. The oxidation of these components enhances the absorption capacity of the scrubbing solution 104 to allow additional odorous vaporous compounds to be absorbed. Depending upon the magnitude of the oxidation of the odorous vaporous compounds, the scrubbing solution 104 may contain byproducts from the oxidation reactions that are soluble in the scrubbing solution 104 or that may adsorb onto semi-colloidal particles formed in the scrubbing solution 104 as described further below.

It should be appreciated that at the start of the process the contents of the sump 112 may be essentially makeup water until the process has completed several cycles in which the scrubbing solution 104 has been contacted the gas stream 102 to reach steady-state. However, during steady-state operation, various components are added to the scrubbing solution to maintain its absorption capacity. Specifically, as the scrubbing solution 104 is pumped from the sump 112 to the spray nozzles 118, various chemical components can be added to the scrubbing solution 104.

Aqueous hydrogen peroxide and any other additives can be added to the scrubbing solution 104 in the recycle line 116. The hydrogen peroxide 122 can be delivered from a source container 124 through a feed line 126 into the recycle line 116 using a pump 128. It should be appreciated that the hydrogen peroxide 122 is added upstream of the recycle pump 114, although, as discussed below, the hydrogen peroxide 122 may be added downstream of the recycle pump 114. In some embodiments in which the hydrogen peroxide is added downstream of the recycle pump 114, any hydrogen peroxide decomposition additive may be added downstream of the point where the hydrogen peroxide 122 is added. Although it should be appreciated that the hydrogen peroxide decomposition additive can be added upstream or downstream of the point where the hydrogen peroxide 122 is added.

The concentration of hydrogen peroxide 122 in the source container 124 should be chosen to allow safe handling given the equipment in use and to provide sufficient concentration for the needs of the wet scrubbing system 100. Although the concentration of hydrogen peroxide 122 in the source container 124 may be selected within a wide range, specific embodiments will range between about 35% to about 50% by weight in an aqueous solution, as these ranges are currently industrially available and legally transportable. In a preferred embodiment, the concentration is about 50% by weight in aqueous solution. In other embodiments, the concentration is about 70% by weight in aqueous solution.

The hydrogen peroxide decomposition additive 130, or a mixture of multiple hydrogen peroxide decomposition additives, is delivered from a source container 132 through a feed line 134 into the recycle line 116 using a pump 136. Upon the addition of the hydrogen peroxide decomposition additive 130 to the recycle line 116 and its inherent mixing with the scrubbing solution 104 in the recycle line 116, the decomposition of at least a portion of the hydrogen peroxide to hydroxyl radicals is catalyzed and occurs within the recycle line 116. The scrubbing solution 104 comprising the hydroxyl radicals is then delivered to the scrubber 106 and the packing 108 through the spray nozzles 118. In one embodiment, the hydrogen peroxide decomposition additive produces predominantly hydroxyl radicals; however, it is not necessary that all of the hydrogen peroxide decompose to hydroxyl radicals or that the decomposition itself only produce hydroxyl radicals. Depending upon the amount of hydroxyl radicals produced, which can be determined based upon the removal efficiency of the odorous vaporous compounds from the gas stream 102, the rate and amount of hydrogen peroxide decomposition additive delivered to the recycle line 116 can be adjusted.

Since the decomposition of at least a portion of the hydrogen peroxide to hydroxyl radicals occurs upon the addition of the hydrogen peroxide decomposition additive 130 to the scrubbing solution 104, it is preferable to add the hydrogen peroxide decomposition additive 130 downstream of the recycle pump 114. This reduces wear on the recycle pump 114 caused by the decomposition product of hydrogen peroxide, e.g., the hydroxyl radicals. However, it should be appreciated that the hydrogen peroxide decomposition additive 130 may be added upstream of the recycle pump 114.

In some embodiments, the hydrogen peroxide decomposition additive is a catalyst that catalyzes the decomposition of hydrogen peroxide to hydroxyl free radicals. Generally, the catalyst is selected relative to the gas stream being treated and the specific gaseous components to be removed so as to generate an aqueous hydrogen peroxide composition having an optimal concentration of hydroxyl free radicals. The catalyst is also selected with a view toward safety and effectiveness. The concentration of the catalyst used will vary depending upon the particular catalyst chosen. Typically, the catalyst will be delivered using an aqueous solution as described above, although for some catalysts, such as ozone and certain of the group VII elements (discussed further below), a direct gaseous addition will be necessary.

In one embodiment, the hydrogen peroxide decomposition additive used is ferrous sulfate. In aqueous media, ferrous ion decomposes hydrogen peroxide in the following manner:

$$Fe^{2+}+H_2O_2 \rightarrow Fe^{3+}+OH^-+OH^*$$

It should be appreciated that the solubility limit of the catalyst presents an upper bound on concentration of the catalyst in the source container 132. In the case of ferrous sulfate, the concentration may be selected within a wide range with specific embodiments within the range between about 20% to about 38% by weight in aqueous solution. In a preferred embodiment the concentration of ferrous sulfate is about 38% by weight in aqueous solution. In this embodiment, the aqueous hydrogen peroxide composition may be added as a 50% by weight hydrogen peroxide solution in its source container.

The ratio by weight of the hydrogen peroxide solution to the ferrous sulfate, based on a 50% by weight hydrogen peroxide solution and a 38% by weight ferrous sulfate solution should be within the range between about 1:1 to about 100:1, within the range between about 2:1 to about 50:1, or within the range between about 5:1 to about 15:1. The higher the ferrous sulfate ratio the more the decomposition reaction is driven to producing hydroxyl free radicals. The ratio can be as high as one part 50% by weight hydrogen peroxide solution to ten parts 38% ferrous sulfate solution, but in this case an extreme amount of heat is generated. While this amount of heat may be acceptable in some settings, it may not be desirable in others.

It should be appreciated that the use of highly electronegative hydroxyl radicals is capable of a much greater decomposition of odor-causing molecules than any composition known in the art. Further, the use of some of the hydrogen peroxide decomposition additives, particularly, ferrous sulfate, not only reduces the hydrogen peroxide to hydroxyl radicals but also introduces a semi-colloidal substrate into the aqueous media that is capable of effectively adsorbing odorous vaporous compounds.

Other additives that act as catalysts, other than ferrous sulfate, may be used alone or in combination with ferrous sulfate. In one embodiment, the catalytic additive may be any element chosen from elements in groups 3B, 4B, 5B, 6B, 7B, 8B, 1B, and 2B of the Periodic Table of Elements and may include combinations thereof. It will be readily apparent to one of skill in the art that the additive(s) selected from these elements would be chosen based upon cost, speed of reaction or catalytic effectiveness, and environmental impact. Among these elements, iron and its conjugates are the cheapest, most readily available, and of the lowest environmental impact.

The "d" block transition elements, characterized by the "d" electrons in their valence shell, and combinations thereof, may also be used. For example, the additive may be cobalt. In one embodiment, the aqueous hydrogen peroxide composition may be formed using an amount of cobalt within the range between about 0.5% wt/wt % to about 1% wt/wt % of the total aqueous hydrogen peroxide composition. Or, the amount of cobalt may be between about 0.5% wt/wt % to about 1% wt/wt % of a solution comprised of cobalt and a 50% by weight hydrogen peroxide solution. In another embodiment, the additive may be any element selected from elements in Group 7A of the Periodic Table of Elements and combinations thereof, for example, fluorine.

In one embodiment, the hydrogen peroxide decomposition additive may be ozone. Using ozone as the additive to catalyze the decomposition of the hydrogen peroxide provides numerous advantages. In particular, using ozone allows for operation at higher pH because the ozone is not as solubility limited at higher pH compared to the hydrogen peroxide decomposition additives that comprise metals. As discussed below, the solubility of a metal-based decomposition additive typically decreases at higher pH, but a chelating agent may be used to enhance its solubility. The use of ozone, however, may displace the need to use a chelating agent in combination with a metal-based decomposition, thereby allowing operation at higher pH. As noted above, operation at higher pH provides the scrubbing solution with a greater capacity to absorb acidic odorous vaporous compounds from the gas stream to be treated, thereby increasing the removal efficiency of the process. Accordingly, when using ozone, because solubility of a metal-based catalytic additive is not an issue, the pH of the scrubbing solution may be increased. The particular pH used in operation can be determined based upon factors such as the type and concentration of the odorous vaporous components in the gas stream and the operating conditions of the scrubber, such as gas rate and the flow rate of the scrubbing solution. Generally, it should be appreciated that virtually any pH above, for example, 5.0, may be used.

When using ozone very poor gas transfer to liquid media has been observed in the art. As part of the present invention, use of a regenerative turbine pump, for example, a Burks regenerative turbine pump manufactured by Burks Manufacturing, can be used as the recycle pump to provide sufficient to excellent mixing of the ozone with the scrubbing solution in the recycle line. Referring back to FIG. 1, such a regenerative turbine pump can be used as the recycle pump 114 in the recycle line 116. In this case, the hydrogen peroxide is added as shown in FIG. 1 upstream of, or on the vacuum side, of the regenerative turbine pump. An ozone/air mixture can then be added to an inlet port pre-built on the vacuum side of the regenerative turbine pump. The resulting liquid discharged from the regenerative turbine pump provides a well mixed stream. In particular, pressurizing the discharge side of the pump to a minimum of 100 psi by using a pinch valve (not shown) gives sufficient gas transfer of the ozone to the liquid media in the recycle line. It will be appreciated that this pinch valve may be controlled using the same control system that regulates the addition of the other additives shown in FIG. 1. It should be appreciated that in some embodiments, the ozone may be added either upstream or downstream of the recycle pump or in any other manner to maximize the transfer of the ozone into the liquid phase and the decomposition of the hydrogen peroxide.

More particularly, as the scrubbing solution, enriched with hydrogen peroxide (due to the addition of hydrogen peroxide from the hydrogen peroxide source container 124), enters the vacuum side of the regenerative turbine pump, the air/ozone mixture is introduced through a pre-machined air port. Intense shear is developed inside the regenerative turbine pump that breaks the ozone/air mixture into microbubbles entrained in the scrubbing solution. The discharge from the regenerative turbine pump is pressurized to approximately 100 psi through a pinch valve assembly, ensuring solubilization of the ozone into the scrubbing solution enriched with hydrogen peroxide, but noting that lower pressures may be used. This allows for the efficient decomposition of the hydrogen peroxide by the ozone into hydroxyl radicals.

The system and process of the embodiment of FIG. 1 may also include a pH control loop to measure the pH of the scrubbing solution 104 in the recycle line 116 and, in response, to regulate the addition of an acid or base 138 into the recycle line 116 to maintain the pH of the scrubbing solution 104 within a preferred pH range or at a specific pH.

In such an embodiment, a sidestream 140 of scrubbing solution 104 is taken from the recycle line 116 and passed by a pH probe 142 and then returned to the scrubber 106. The pH probe 142 measures the pH of this sidestream 140 and communicates the measured pH to a pH controller 144. The pH controller 144 then regulates, as needed, the addition of an acid or base 138 from an acid or base source container 146 into the recycle line 116 through feed line 148 using a pump 150. In one embodiment, the acid or base 138 is added upstream of the recycle pump 114. However, it may also be added to the sidestream 140 or downstream of the recycle pump 114. In another embodiment, the acid or base 138 can be added directly to the sump 112.

Through the addition of acid or base using the pH control loop, the pH of the scrubbing solution 104 in the recycle line 116 can be maintained at a level that maximizes the decomposition of the hydrogen peroxide by the hydrogen peroxide decomposition additive that catalyzes such decomposition and that provides for the greatest absorption capacity of the scrubbing solution (e.g., maintaining a given pH in the scrubbing solution that provides the highest level of solubility for one or more odorous vaporous compounds in the scrubbing solution). This, in turn, allows the removal of the odorous vaporous compounds from the gas stream to be optimized. One of skill in the art will appreciate that the optimal pH to be used will be dependent upon the particular gaseous components to be removed and oxidized and their respective properties and concentration in the gas stream 102, as well as the composition of the scrubbing solution 104 and operating conditions of the scrubber 106, such as the gas and scrubbing solution flow rates. For example, in removing hydrogen sulfide, its solubility is pH dependent and increases with increasing pH above about pH 5 to about pH 9.5. Accordingly, this solubility property needs to be taken into account in selecting an operating pH of the scrubbing solution when removing hydrogen sulfide. Additionally, the solubility of the decomposition additive, particularly a metal-based additive (discussed below), relative to the pH of the scrubbing solution needs to be taken into account. Typically, metal-based additives are less soluble at higher pH, so that the pH may need to be controlled at a lower level to maintain an adequate concentration of such an additive in solution to catalyze the decomposition of the hydrogen peroxide.

As noted above, in some embodiments, the scrubbing solution 104 may include additional additives, including wetting agents, dispersant polymers, and/or chelating agents (discussed further below). Addition of these additives would be made similar to the addition of the additive for catalyzing the decomposition of the hydrogen peroxide discussed above. Thus, there may be separate source containers to enable the regulated delivery of these additional additives in aqueous form to the recycle line 116. Preferably, these additional additives are added on the downstream side of the recycle pump 114; however, these additives could be added at other locations, including, for example, anywhere along the recycle line 116 or directly to the sump 112. Additionally, some or all of these other additives may be mixed together and delivered from a single source container. Alternatively, any one or more of these additives may be provided together with one or more other additives. For example, the hydrogen peroxide in its source container 124 may contain any one or more chemically compatible (e.g., resistant to oxidation) additives such as certain chelating agents and/or wetting agents. Of course, the additives may also be provided with the hydrogen peroxide decomposition additive 130 from its source container 132 and/or from a source container 150 containing acid or base 138.

In one embodiment, a nonionic wetting agent may be added to the scrubber or to the scrubbing solution to enhance its activity by allowing further penetration of the oxidizing agent into crevices of bacterial forms of odorous and/or noxious components or compounds. While the exact mechanism is not known, it is believed that certain nonionic surfactants, i.e., wetting agents, assist in the degradation of bacterial cell walls allowing the scrubbing solution to more readily kill the bacteria in the medium.

Preferred wetting agents are octylphenols, ethylene oxide block copolymers, propylene oxide block copolymers, and combinations thereof. The determining factors for wetting agent choice is organic loading of the effluent, i.e., the level of proteins or starches in the effluent, cleanliness of the system being treated, i.e., the amount of deposits and slime on the surfaces of the scrubber tank or sump and packing, as well as need for defoaming capabilities. In one embodiment, the wetting agent, as 100% active material, is present in an amount up to about 10% by weight of the scrubbing solution (in the scrubber or as additives to the recycle line), an amount up to about 5% by weight of the scrubbing solution, or an amount up to about 1% by weight of the scrubbing solution.

In another embodiment, a low molecular weight dispersant polymer may be added to the scrubber or to the scrubbing solution in order to prevent iron and other particle agglomeration in the aqueous media as well as to prevent iron and organic deposition in lower liquid flow areas. In one embodiment, the average molecular weight of these low molecular weight dispersants is within the range between about 1,000 to about 22,000 or within the range between about 1,000 to about 9,000. These low molecular weight dispersants may be, but are not limited to, homopolymers of acrylic acid, methacrylic acid, acrylamide, copolymers and terpolymers acrylates, methacrylates, acrylamide, AMPS (2-acrylamido-2-methyl propane sulfonic acid), and combinations thereof. For example, a dispersant resistant to oxidation may be desirable in situations where sulfur-based compounds that are formed as a result of operation at higher pHs and interaction with a metal-based decomposition additive in which insoluble agglomerations, such as zinc sulfate, are formed.

The low molecular weight dispersant polymer is added on a weight percent basis (i.e., wt/wt % of the total composition weight of the aqueous hydrogen peroxide composition in the scrubber or as additives to a scrubber sidestream). In one embodiment, the percentage of the low molecular weight dispersant in the scrubbing solution is within the range between about 0.5% active wt/wt % to about 10% active wt/wt % of the total scrubbing solution, within the range between about 0.5% active wt/wt % to about 5% active wt/wt % of the total scrubbing solution, or within the range between about 0.5% active wt/wt % to about 2% active wt/wt % of the total scrubbing solution.

In another embodiment, a chelating agent may be added to the scrubbing solution. As earlier discussed, a semi-colloidal metal complex may form during the oxidation process, and in some instances, the development of this colloidal metal complex is undesirable. A chelating agent may be added to prevent the formation of metal hydroxides or other insoluble metal complexes. In one embodiment, the chelating agents may be organic acids such as gluconic acids, citric acids, glycolic acids, lactic acids, and combinations thereof. It will be appreciated that a large number of chelating agents may also be used and their selection apparent to those of skill in the art; however, the chelating agent should not be of such potent chelating ability as to prevent the availability of the metal complex for decomposition purposes.

A chelating agent may also be added to enhance the solubility of the hydrogen peroxide decomposition additive or catalyst. This may, in some embodiments, allow for operation at higher pH. As noted above, higher pH increases removal of the odorous vaporous compounds in the gas compared to lower pH operation. It should be appreciated, however, that a chelating agent may be used to enhance the solubility of the hydrogen peroxide decomposition additive in some embodiments where increasing the pH may not be necessary.

Generally, chelating agents can be selected based upon the particular hydrogen peroxide decomposition additive being used. For example, chelating agents known in the art may be used to increase the solubility of metal-based hydrogen peroxide decomposition additives, such as ferrous ion and other metal complexes. In addition, ferric ($Fe^{3+}$) ion may be used as the hydrogen peroxide decomposition additive to decompose hydrogen peroxide to hydroxyl radicals, and chelating agents may be added to increase the solubility of the ferric ion, thereby increasing the production of hydroxyl free radicals and allowing for operation at a higher pH. Chemical Treatment of Pesticide Wastes—Evaluation of Fe(III) Chelates for Catalytic Hydrogen Peroxide Oxidation of 2,4-D at Circumneutral pH, Sun et al., J. Agric. Food Chem., 1992, 40, 322-327, which is incorporated by reference herein in its entirety, describes several chelating agents that may be used to solubilize ferric ion. Such chelating agents that showed "high" catalytic activity and that may be used in the present invention include: aminopolycarboxylates, such as nitrilotriacetic acid and hydroxyethyliminodiacetic acid; N-heteroxcyclic carboxylates, such as picolinic acid; polyhydroxy aromatics, such as gallic acid; and other compounds, such as rhodizonic acid, tetrahydroxy-1,4-quinone, and hexaketocyclohexane. These chelating agents may be used separately; however, it may be possible to use mixtures of these chelating agents as well. In other embodiments, the chelating agent comprises methylglycinediacetate or trisodium methylglycinediacetate (available as TRILON M from BASF Corporation, believed to have been developed as an environmentally friendly alternative to nitrilotriacetic acid or "NTA") or methylglycinediacetic acid.

It should be appreciated that the chelating agent and the hydrogen peroxide decomposition additive, such as ferrous ion or ferric ion (which may be added, for example, as ferric sulfate) may be mixed before use to allow for chelation. For example, referring to FIG. 1, the chelating agent and the ferric ion may be chelated prior to placing such a mixture in the source container 132 for the hydrogen peroxide decomposition additive. In this case, the selection of the hydrogen peroxide decomposition additive and chelating agent can be based upon the specific application or particular gaseous components to be removed and the desired operating pH. By mixing the hydrogen peroxide decomposition additive and the chelating agent prior to use, this mixture is essentially "tailor-made" and is ready for immediate use in the particular application at issue. In fact, this mixture can be prepared remote from the facility where it will be used and shipped to that facility for immediate use. In some embodiments, methylglycinediacetate or trisodium methylglycinediacetate can be mixed with a source of ferric ion, such as a ferric salt solution, to produce a ferric chelate, ferric methylglycinediacetate, as described in U.S. Pat. No. 6,960,330 to Cox, which is incorporated herein by reference in its entirety.

Alternatively, the hydrogen peroxide decomposition additive and the chelating agent may be added separately to the hydrogen peroxide decomposition additive source container 132, thereby allowing for in-situ chelation in the source container 132. In this case, consideration must be given to the rate at which this solution is added to the recycle line 116 to provide sufficient time for chelation to occur. One of skill in the art will appreciate the conditions necessary to chelate, including use of the proper pH, which may be in some embodiments, for example, pH 6. Alternatively still, the chelating agent may be added through the use of a separate source container (not shown) in a manner similar to that of the hydrogen peroxide decomposition additive source container 132. Further, the use of a separate source container for the chelating agent may be used to dispense the chelating agent into the recycle line 116 either upstream or downstream of the recycle pump 114; however, it is preferable to dispense the chelating agent into the recycle line 116 as closely as possible to the point where the decomposition additive is added to the recycle line 116.

As noted above, use of a chelating agent to increase the solubility of the hydrogen peroxide decomposition additive (for example, metal-based additives and, in particular, ferrous or ferric ions) allows for operation at a higher pH in the scrubbing solution that is fed to the scrubber. Operation at higher pH increases the capacity of the scrubbing solution to absorb additional acidic gases, thereby increasing the removal efficiency of the process. It should be appreciated that the specific pH used will be dependent upon the particular gaseous components to be removed from the gas stream and, correspondingly, may include a wide range of pHs. In some embodiments, it may be desirable to not change the operating pH significantly or at all upon the addition of a chelating agent.

The system and process of the embodiment of FIG. 1 may also include a source container 152 to deliver other additives, such as a biocide 154 into the scrubber 106. In one embodiment, the additional additive 154 is added to the scrubber 106 through a feed line 156 to the recycle line 116 using a pump 158. In this case, the additional additive 154 may be added upstream or downstream of the recycle pump 114. In either case, the additional additive 154 will enter the scrubber 106 with the scrubbing solution 104. The additional additive 154 can be added continuously or semi-continuously or a designated intervals as necessary. In another embodiment, the additional additive 154 can be added batch-wise to shock-treat the system.

According to another embodiment, the additional additive 154 may be combined with the aqueous hydrogen peroxide 122 in its source container 124 and added to the recycle line 116 with the hydrogen peroxide 122. In yet another embodiment, the additional additive 154 may be combined with the acid or base 138 in its source container 150 and added to the recycle line 116 with the acid or base 138. In another embodiment, the additional additive 154 may be combined with the decomposition additive 130 in its source container 132 and added to the recycle line 116 with the hydrogen peroxide decomposition additive 130. The additional additive 154 may also be added directly to the sump 112.

In some embodiments in which the additional additive 154 is a biocide, such may be added in the various methods described above as an aqueous solution. In other embodiments, a tablet form of a biocide, such as bromide, is used and can be added directly to the sump 112. It should be appreciated that in those embodiments in which the biocide is combined with another material before being added to the recycle line 116 the biocide may be added directly to the respective source container of the other material or added to its own source container 152 and from there added through its feed line 156 to the appropriate other source container through separate feed lines 160, 162, 164. Other aspects regarding the use of a biocide are described in U.S. Patent Application Publication No. US 2012/0087827, entitled "Method and Apparatus for Treating Industrial Gas Streams and Biological Fouling," which is incorporated by reference herein in its entirety.

As described above, a biocide is added to the scrubber 106 to treat biofouling that may occur in the scrubber 106, particularly in the packing 108 or in the sump 112. According to one embodiment, the amount of biocide added is the amount necessary to maintain a residual concentration in the scrubbing solution 104. Depending upon the biocide used, manufacturer's recommendations for the amount of biocide necessary may also be used. Further, certain operating parameters can be measured to determine whether the amount of biocide added or the concentration of biocide needs to be altered. For example, one technique for determining whether an accumulation of biofouling exists in the scrubber 106 is by monitoring the gas pressure differential across the packing 108. A drop in the gas pressure across the packing 108, or an increase in the gas differential, may be used to indicate an increase in biofouling in the packing 108. In this case, additional biocide may be added or the residual biocide concentration may be increased.

Generally, any biocide may be used. In one embodiment, the biocide is quaternary ammonium. In some embodiments, the residual concentration of quaternary ammonium in the scrubbing solution is about 6 to about 7 parts per billion (ppb). In another embodiment, the biocide is not an oxidizer. Such non-oxidizers include dibromo nitrilopropionamide (DBNPA), 2,2 dibromo-3-nitrilopropionamide, gluteraldehyde, a carbamate, mercaptobenzothiazole (MBT), or isothiazolinone. In some embodiments, the biocide is a mixture of alkyl dimethylbenzylammonium chloride and alkyl dimethylethylbenzyl-ammonium chloride, including, in some embodiments, a mixture of these two compounds at 25% by weight.

It should be appreciated that the addition rates of any of the foregoing materials to the recycle line 116, the sump 112, or to the scrubbing solution 104 in general can be regulated to achieve the desired feed rate and concentration in the scrubbing solution 104 by any means known in the art, such as control valves, flow meters, or variable speed pumps. Further, the equipment for feeding these components may by stand-alone or independent or be incorporated as part of a larger control system, particularly in the case where the system includes more than one scrubber. It will be appreciated that other embodiments may be utilized in which the components of the scrubbing solution 104 are added at different locations within the system, including different locations along the recycle line 116 or directly to the sump 112.

One of skill in the art will appreciate that the actual composition of the scrubbing solution in the recycle line and, specifically, the concentration of hydrogen peroxide, the decomposition additive, and hydroxyl free radicals therein, is determined based upon the composition of the gas stream entering the scrubber and the specific gaseous components to be removed, as well as the scrubber operating conditions. At a given set of scrubber operating conditions (such as the gas flow rate and concentration of odorous and/or noxious components and the scrubbing solution flow rate through the scrubber), the addition rate of either or both of the hydrogen peroxide and the decomposition additive may be adjusted to provide the necessary production of hydroxyl free radicals to achieve the desired removal rate of odorous and/or noxious components or compounds. Of course, the concentration of the hydrogen peroxide and the decomposition additive in their respective source containers may be adjusted to achieve the desired rate of addition of each to the system taking into account overall water balance considerations.

The various embodiments described above have been primarily with reference to removal of odorous vaporous compounds from a gas stream in which the odorous vaporous compounds are absorbed and oxidized during contact with a scrubbing solution comprising hydrogen peroxide and hydroxyl radicals to produce a substantially non-odor offensive, environmentally acceptable byproduct. It should be appreciated, however, that various oxidizers or solutions containing oxidizers may be used. For example, oxidizing compounds such as chlorine gas, sodium hypochlorite, hypobromous acid, chlorine dioxide, hydrogen peroxide, peroxy acids, ozone, and permanganate may be used alone or in combination.

In addition, various embodiments have been described above in the context of the use of a wet scrubber system using a single packed column with a single integrated sump. It should be appreciated that other gas/liquid contactors may be used in the wet scrubber system. For example, spray towers, venturi spray condensers, or a combination of spray towers and packed columns may be used. Further, counter-current scrubbers, where the direction of the gas flow is opposite the direction of the liquid flow; co-current scrubbers, where the direction of the gas flow is in the same direction as the liquid flow; and cross-flow scrubbers, where the direction of the gas flow is at an angle to the direction of the liquid flow; may be used. In addition, it should be appreciated that more than one sump may be used for a single scrubber or, alternatively, one sump may be used for more than one scrubber. Further, it should be appreciated that the sump does not necessarily need to be integral to the gas/liquid contactor and may be a separate tank, provided that appropriate gas seals are in place.

It should also be appreciated that more than one gas/liquid contactor may be used in a single system. Such gas/liquid contactors may be of the same or various types and may be configured to operate in series or in parallel. Each gas/liquid contactor could also have its own sump or multiple gas/liquid contactors may share the same sump. In using more than one gas/liquid contactor with one or more sumps, it is possible to utilize one set of source containers for hydrogen peroxide, additives, and any acid or base required for pH control, or separate source containers may be used in connection with a given one or more gas/liquid contactors.

Figure 2:
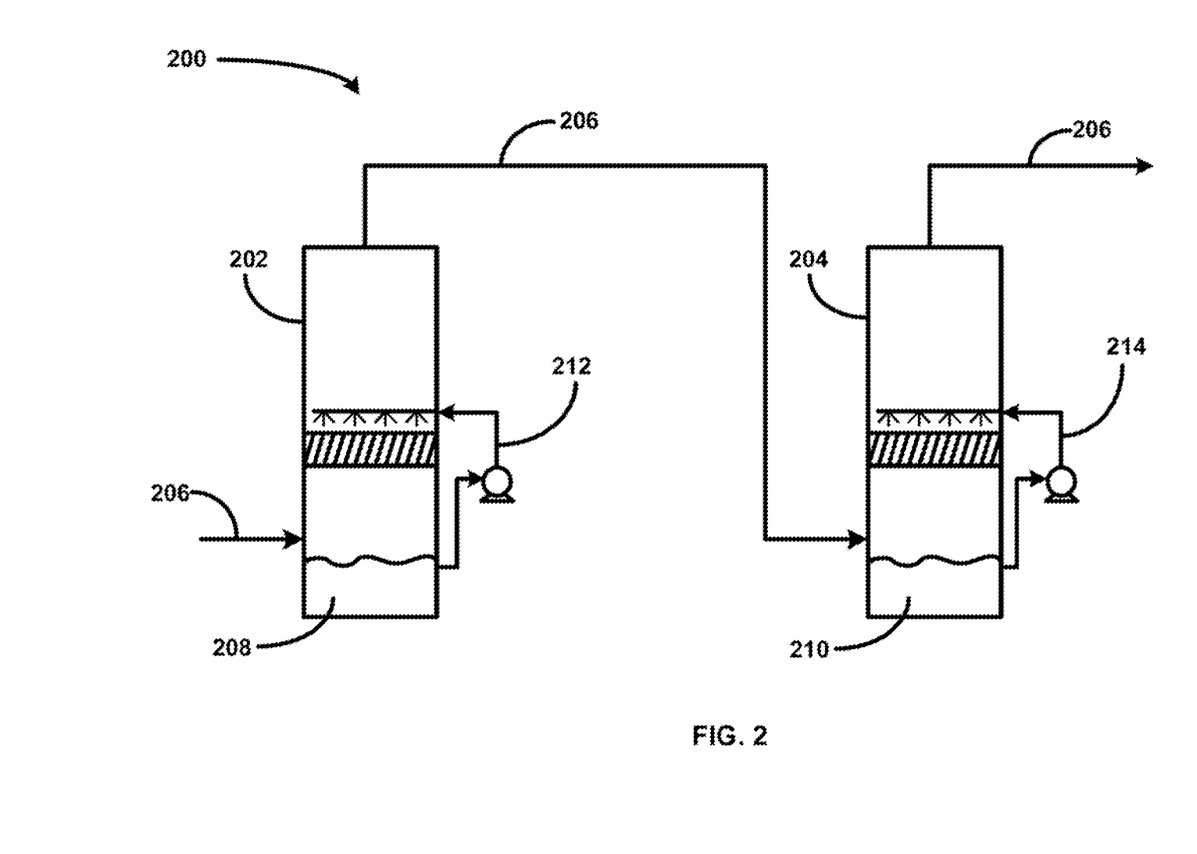
FIG. 2 illustrates a series of scrubbers and related process equipment for implementing one embodiment of the present invention.

FIG. 2 illustrates a series of gas/liquid contactors and related process equipment for implementing one embodiment of the present invention. In this process 200, two gas/liquid contactors 202, 204, shown as packed bed scrubbers, are used in series to remove one or more odorous vaporous compounds from a gas stream 206. In this embodiment, the gas stream 206 comprising one or more odorous vaporous compounds enters the first packed bed scrubber 202, where one or more odorous vaporous compounds are removed from the gas stream 206. Upon exiting the first packed bed scrubber 202, the gas stream 206 is passed to the second packed bed scrubber 204 where one or more odorous vaporous compounds are removed from the gas stream 206. It should be appreciated that the particular odorous vaporous compounds removed in each scrubber 202, 204 may be the same or different. For example, it may be possible to remove a portion of a particular odorous vaporous compound in the first scrubber 202 and then remove an additional portion of that same odorous vaporous compound in the second scrubber 204. Alternatively, it may be possible to remove a portion of a particular odorous vaporous compound in the first scrubber 202 and then remove a portion of a different odorous vaporous compound in the second scrubber 204. It may also be possible to remove a portion of one particular odorous compound and a second one or more of another particular odorous vaporous compound in the first scrubber 202 and then remove an additional portion of one of the same odorous vaporous compounds in the second scrubber 204 as well as a portion of yet another different odorous vaporous compound that may not have been removed in the first scrubber 202.

Each of the packed bed scrubbers 202, 204 are similar to the gas/liquid contactor described in connection with FIG. 1. In addition, each of these packed bed scrubbers 202, 204 may be operated in the same manner as that described in connection with FIG. 1, including with respect to the addition of hydrogen peroxide, a hydrogen peroxide decomposition additive, and other additives. Therefore, the equipment related to the addition of these components to the scrubbing solution in each packed bed scrubber 202, 204 is not shown in FIG. 2. It should be appreciated, however, that although the gas/liquid contactors 202, 204 are shown as packed bed scrubbers, any type of gas/liquid contactor may be substituted for one or both of the packed bed scrubbers 202, 204, such as a spray venturi. Therefore, any combination of gas/liquid contactors may be used. Further, the scrubbing solution used in either scrubber may include any composition of scrubbing solution described above.

In one embodiment, however, the scrubbing solution in one scrubber is controlled at an alkaline pH, and the scrubbing solution in the other scrubber is controlled at an acidic pH. The pH control for each scrubbing solution can be performed in the same manner as described above in connection with FIG. 1. It should be appreciated that the scrubbing solution 208 in the first scrubber 202 may use either an alkaline scrubbing solution or an acidic scrubbing solution with the second scrubber 204 utilizing the opposite scrubbing solution. For example, if an acidic pH scrubbing solution is used in the first scrubber 202, then an alkaline scrubbing solution would be used in the second scrubber 204 and vice versa. It should be appreciated that by utilizing two scrubbers, each with scrubbing solutions at different pHs, different types of odorous vaporous compounds may be absorbed since not all such compounds can be absorbed at the same pH. Accordingly, a larger fraction of all of the odorous vaporous compounds can be removed compared to use of a single gas/liquid contactor.

Although either scrubber may utilize an alkaline or acidic scrubbing solution, the following description will be for a process in which the first scrubber 202 utilizes an alkaline scrubbing solution and the second scrubber 204 utilizes an acidic scrubbing solution. Accordingly, the scrubbing solution 208 in the first scrubber 202 is controlled at an alkaline pH. In some embodiments, the pH of the scrubbing solution 208 in the first scrubber 202 is controlled at a pH of a pH 7.0 or greater. In some embodiments, the pH of this scrubbing solution is controlled at a pH of approximately 7.0, 7.5, 8.0, 8.5, 9.0, 9.2, or 9.5 or higher. As noted above, control of the pH can be done as described above in connection with FIG. 1.

The alkaline scrubbing solution 208 comprises hydrogen peroxide that is fed to the recycle line 212 as described above in connection with FIG. 1. In addition, optionally, a hydrogen peroxide additive and/or a chelating agent may be added to the scrubbing solution 208 as well. Therefore, it should be appreciated that the alkaline scrubbing solution may comprise a solution of only hydrogen peroxide; a solution of hydrogen peroxide and a hydrogen peroxide decomposition additive, such as ferrous or ferric ion or any of the other hydrogen peroxide decomposition additives described above, in which case the scrubbing solution will contain the reaction product or products of the decomposition of the hydrogen peroxide; or hydrogen peroxide, a hydrogen peroxide decomposition additive, and a chelating agent as described above. It should be appreciated that any of the methods described above in connection with FIG. 1 may be used for mixing and adding these components to the scrubbing solution 208. Further, additional additives described above in connection with FIG. 1 may also be used in this embodiment, and any of the methods described above in connection with FIG. 1 may be used for mixing and adding these components to the scrubbing solution 208.

The scrubbing solution 210 used in the second gas/liquid contactor 204 is an acidic scrubbing solution and is controlled at an acidic pH. In some embodiments, the pH of this scrubbing solution 210 is controlled at a pH that is less than 7.0, 6.5, 6.0, 5.5, or 5.0 or lower. As noted above, control of the pH can be done as described above in connection with FIG. 1.

The scrubbing solution 210 comprises hydrogen peroxide that is fed to the recycle line 214 as described above in connection with FIG. 1. In addition, optionally, a hydrogen peroxide additive and/or a chelating agent may be added to the scrubbing solution 210 as well. Therefore, it should be appreciated that the acidic scrubbing solution may comprise a solution of only hydrogen peroxide; a solution of hydrogen peroxide and a hydrogen peroxide decomposition additive, such as ferrous or ferric ion or any of the other hydrogen peroxide decomposition additives described above, in which case the scrubbing solution will contain the reaction product or products of the decomposition of the hydrogen peroxide; or hydrogen peroxide, a hydrogen peroxide decomposition additive, and a chelating agent as described above. It should be appreciated that any of the methods described above in connection with FIG. 1 may be used for mixing and adding these components to the scrubbing solution 210. Further, additional additives described above in connection with FIG. 1 may also be used in this embodiment, and any of the methods described above in connection with FIG. 1 may be used for mixing and adding these components to the scrubbing solution 210. Again, it should be appreciated that the first scrubber 202 may utilize an acidic scrubbing solution, as described above, and the second scrubber 204 may utilize an alkaline scrubbing solution as described above.

In one embodiment, the operation of the scrubbers 202, 204 may be reversed temporarily or for a given period of time during which each scrubber 202, 204 uses a scrubbing solution controlled at a pH at which the other scrubber's scrubbing solution was operating. For example, the process 200 shown in Figure may be operated in a manner in which the first scrubber 202 utilizes an alkaline scrubbing solution 208, and the second scrubber 204 utilizes an acidic scrubbing solution 210. After operation in this mode for a given period of time, the operation of the scrubbers 202, 204 is reversed such that the first scrubber 202 utilizes an acidic scrubbing solution 208, and the second scrubber 204 utilizes an alkaline scrubbing solution 210 for another given period of time. After this period of time, the scrubbers 202, 204 may be switched again to utilize a scrubbing solution controlled at the original pH (i.e., the first scrubber 202 would again utilize an alkaline scrubbing solution 208, and the second scrubber 204 would again utilize an acidic scrubbing solution 210).

In one embodiment, the scrubbing solutions may be changed by simply discharging the scrubbing solutions currently being used by each scrubber and starting with fresh or new scrubbing solution now controlled at the pH originally used in the opposite scrubber. It should be appreciated, however, that the operating pH of the respective scrubbing solutions does not necessarily have to be equivalent to that used in the other scrubber prior to switching the operating pH of each scrubbing solution. For example, if the first scrubber was utilizing an alkaline scrubbing solution controlled at pH 9.2 and the second scrubber was utilizing an acidic scrubbing solution controlled at pH 5.0, after starting with new scrubbing solution in each scrubber, such that the first scrubber would be utilizing an acidic scrubbing solution and the second scrubber would be utilizing an alkaline scrubbing solution, the respective new scrubbing solutions in each scrubber do not necessarily have to be controlled at pHs of 9.2 and 5.0 (e.g., the new acidic scrubbing solution in the first scrubber can be controlled at a acidic pH other than 5.0 and the new alkaline scrubbing solution in the second scrubber can be controlled at a alkaline pH other than 9.2). However, in some cases, the pH will be controlled at the same pH originally used in the other scrubber.

It should also be appreciated that the composition of each scrubbing solution does not necessarily have to be the same as the scrubbing solution used in the other scrubber prior to switching the operating pH of each scrubbing solution. For example, if the first scrubber was utilizing a scrubbing solution comprising only hydrogen peroxide and the second scrubber was utilizing a scrubbing solution comprising hydrogen peroxide and a hydrogen peroxide decomposition additive, after starting with new scrubbing solution in each scrubber, the first scrubbing solution could utilize only hydrogen peroxide and is not limited to using hydrogen peroxide and a hydrogen peroxide decomposition additive as was used in the second scrubber prior to switching. However, in some cases, the components used in the respective scrubbing solutions can be the same as used in the other scrubber prior to switching.

It should also be appreciated that the feed lines for the various components added to each scrubbing solution can be piped to allow for feeding to either scrubber. In this manner, the components fed to each scrubbing solution can be easily fed to the opposite scrubber to allow that scrubber to be started with a new scrubbing solution that is now controlled at a different pH. For example, any acids or bases used to control the pH of the scrubbing solutions can be piped to feed to either scrubber recycle line. In this manner, if the first scrubber utilizes an alkaline scrubbing solution to which a base is fed to control the pH at the desired alkaline pH, piping can be used such that the same base can also be fed to the recycle line of the second scrubber such that upon switching the operating pH of the scrubbing solutions, the same base can easily be used to control the pH of the scrubbing solution in the second scrubber at the desired alkaline pH.

This temporary switching of the pH at which each scrubber's scrubbing solution is controlled may provide cleaning benefit for the scrubbers. For example, scale deposits that may have built-up in the first scrubber 202 during operation with an alkaline scrubbing solution may be dissolved and removed during operation with an acidic scrubbing solution. In this case, an acidic scrubbing solution may be used in the first scrubber 202 and an alkaline scrubbing solution may be used in the second scrubber 204 for a given period of time to allow the acidic scrubbing solution to effectively dissolve some or all of the scale deposits in the first scrubber 202. After this period of time, an alkaline scrubbing solution may again be used in the first scrubber 202 and an acidic scrubbing solution may again be used in the second scrubber 204.

It should also be appreciated that the gas stream 306 being fed to the two scrubbers 202, 204 in series may be pre-treated before being fed to these scrubbers. For example, the gas stream may be condensed in one or two stages to condense one or more odorous vaporous compounds. In one embodiment, the gas may be condensed in a first stage to a temperature of approximately 40° C. and then further condensed in a second stage to a temperature of approximately 0° C. The gas stream may then be further treated by passing it through a particulate collection device, such as an electrostatic precipitator, to remove any particulate matter from the gas stream.

It should be appreciated, however, that any scrubbing solution that utilizes any of the oxidizing compounds described above may be used in either or both of the scrubbers used in the process 200 shown in FIG. 2. Further, all of the same additives described above in connection with FIG. 1 can be added to the scrubbing solution for either gas/liquid contactor shown in FIG. 2 if appropriate given the pH and composition of the specific scrubbing solution.

Although the foregoing invention has been described in some detail to facilitate understanding, it will be apparent that certain changes and modifications may be practiced within the scope of the appended claims. Accordingly, the described embodiment is to be considered as illustrative and not restrictive, and the invention is not to be limited to the details given herein, but may be modified within the scope and equivalents of the appended claims.

What is claimed is:

1. A method for reducing the concentration of at least one odorous compound in a gas stream, comprising:
    passing a gas stream comprising at least one odorous compound through a first gas/liquid contactor;
    contacting said gas stream in said first gas/liquid contactor with a first liquid scrubbing solution;
    passing said gas stream from said first gas/liquid contactor through a second gas/liquid contactor; and
    contacting said gas stream in said second gas/liquid contactor with a second liquid scrubbing solution,
    wherein said first liquid scrubbing solution comprises an alkaline liquid scrubbing solution comprising hydrogen peroxide but not a hydrogen peroxide decomposition additive and said second liquid scrubbing solution comprises an acidic liquid scrubbing solution comprising a reaction product of hydrogen peroxide and a hydrogen peroxide decomposition additive, or wherein said first liquid scrubbing solution comprises an acidic liquid scrubbing solution comprising a reaction product of hydrogen peroxide and a hydrogen peroxide decomposition additive and said second liquid scrubbing solution comprises an alkaline liquid scrubbing solution comprising hydrogen peroxide but not a hydrogen peroxide decomposition additive.

2. The method of claim 1, wherein said acidic liquid scrubbing solution further comprises a pH of less than 5.0.

3. The method of claim 1, wherein said acidic liquid scrubbing solution further comprises a chelating agent.

4. The method of claim 1, wherein said alkaline liquid scrubbing solution further comprises a pH greater than 8.5.

5. The method of claim 1, wherein said alkaline liquid scrubbing solution further comprises a chelating agent.

6. The method of claim 1, wherein said contacting said gas stream in said first gas/liquid contactor with said first liquid scrubbing solution and said contacting said gas stream in said second gas/liquid contactor with said second liquid scrubbing solution are performed for a first period of time and wherein said first liquid scrubbing solution comprises said alkaline liquid scrubbing solution comprising said hydrogen peroxide and said second liquid scrubbing solution comprises said acidic liquid scrubbing solution comprising said reaction product of said hydrogen peroxide and said hydrogen peroxide decomposition additive, and further comprising:
    contacting said gas stream in said first gas/liquid contactor with a third acidic liquid scrubbing solution after said first period of time; and
    contacting said gas stream in said second gas/liquid contactor with a fourth alkaline liquid scrubbing solution after said first period of time.

7. The method of claim 6, wherein said contacting said gas stream in said first gas/liquid contactor with said third liquid scrubbing solution and said contacting said gas stream in said second gas/liquid contactor with said fourth liquid scrubbing solution are performed for a second period of time, and further comprising:
    contacting said gas stream in said first gas/liquid contactor with said first liquid scrubbing solution after said second period of time;
    contacting said gas stream in said second gas/liquid contactor with said second liquid scrubbing solution after said second period of time.

8. The method of claim 1, wherein said contacting said gas stream in said first gas/liquid contactor with said first liquid scrubbing solution and said contacting said gas stream in said second gas/liquid contactor with said second liquid scrubbing solution are performed for a first period of time and wherein said first liquid scrubbing solution comprises said acidic liquid scrubbing solution comprising said reaction product of said hydrogen peroxide and said hydrogen peroxide decomposition additive and said second liquid scrubbing solution comprises said alkaline liquid scrubbing solution comprising said hydrogen peroxide, and further comprising:
    contacting said gas stream in said first gas/liquid contactor with a third alkaline liquid scrubbing solution after said first period of time; and
    contacting said gas stream in said second gas/liquid contactor with a fourth acidic liquid scrubbing solution after said first period of time.

9. The method of claim 8, wherein said contacting said gas stream in said first gas/liquid contactor with said third liquid scrubbing solution and said contacting said gas stream in said second gas/liquid contactor with said fourth liquid scrubbing solution are performed for a second period of time, and further comprising:
    contacting said gas stream in said first gas/liquid contactor with said first liquid scrubbing solution after a second period of time; and
    contacting said gas stream in said second gas/liquid contactor with said second liquid scrubbing solution after said second period of time.

10. A method for reducing the concentration of at least one odorous compound in a gas stream, comprising:
    passing a gas stream comprising at least one odorous compound through a first gas/liquid contactor;
    contacting said gas stream in said first gas/liquid contactor with an acidic liquid scrubbing solution;
    passing said gas stream from said first gas/liquid contactor through a second gas/liquid contactor; and
    contacting said gas stream in said second gas/liquid contactor with an alkaline liquid scrubbing solution comprising hydrogen peroxide without a hydrogen peroxide decomposition additive in said second gas/liquid contactor, wherein said acidic liquid scrubbing solution comprises hydrogen peroxide and a hydrogen peroxide decomposition additive.

11. The method of claim 10, wherein said acidic liquid scrubbing solution comprises a chelating agent and a biocide to reduce biofouling in said first gas/liquid contactor.

12. A method for reducing the concentration of at least one odorous compound in a gas stream, comprising:
  passing a gas stream comprising at least one odorous compound through a first gas/liquid contactor;
  contacting said gas stream in said first gas/liquid contactor with an alkaline liquid scrubbing solution comprising hydrogen peroxide without a hydrogen peroxide decomposition additive;
  passing said gas stream from said first gas/liquid contactor through a second gas/liquid contactor; and
  contacting said gas stream in said second gas/liquid contactor with an acidic liquid scrubbing solution in said second gas/liquid contactor, wherein said acidic liquid scrubbing solution comprises hydrogen peroxide and a hydrogen peroxide decomposition additive.

13. A method for reducing the concentration of at least one odorous compound in a gas stream, comprising:
  passing a gas stream comprising at least one odorous compound through a first gas/liquid contactor;
  contacting said gas stream in said first gas/liquid contactor with a first alkaline liquid scrubbing solution comprising hydrogen peroxide for a first length of time;
  passing said gas stream from said first gas/liquid contactor through a second gas/liquid contactor;
  contacting said gas stream in said second gas/liquid contactor with a first acidic liquid scrubbing solution comprising a reaction product of hydrogen peroxide and a hydrogen peroxide decomposition additive during said first length of time;
  contacting, after said first length of time, said gas stream in said first gas/liquid contactor with a second acidic liquid scrubbing solution comprising hydrogen peroxide and a hydrogen peroxide decomposition additive for a second length of time; and
  contacting, after said first length of time, said gas stream in said second gas/liquid contactor with a second alkaline liquid scrubbing solution comprising hydrogen peroxide during said second length of time.

14. The method of claim 13, further comprising:
  contacting said gas stream in said first gas/liquid contactor with said first alkaline liquid scrubbing solution after said second length of time; and
  contacting said gas stream in said second gas/liquid contactor with said first acidic liquid scrubbing solution after said second length of time;
  wherein said second acidic scrubbing solution is the same as said first acidic scrubbing solution and wherein said second alkaline scrubbing solution is the same as said first alkaline scrubbing solution.

15. A method for reducing the concentration of at least one odorous compound in a gas stream, comprising:
  passing a gas stream comprising at least one odorous compound through a first gas/liquid contactor;
  contacting said gas stream in said first gas/liquid contactor with a first acidic liquid scrubbing solution comprising a reaction product of hydrogen peroxide and a hydrogen peroxide decomposition additive for a first length of time;
  passing said gas stream from said first gas/liquid contactor through a second gas/liquid contactor;
  contacting said gas stream in said second gas/liquid contactor with a first alkaline liquid scrubbing solution comprising hydrogen peroxide during said first length of time;
  contacting, after said first length of time, said gas stream in said first gas/liquid contactor with a second alkaline liquid scrubbing solution comprising hydrogen peroxide for a second length of time; and
  contacting, after said first length of time, said gas stream in said second gas/liquid contactor with a second acidic liquid scrubbing solution comprising hydrogen peroxide and a hydrogen peroxide decomposition additive during said second length of time.

16. The method of claim 15, further comprising:
  contacting said gas stream in said first gas/liquid contactor with said first acidic liquid scrubbing solution after said second length of time; and
  contacting said gas stream in said second gas/liquid contactor with said first alkaline liquid scrubbing solution after said second length of time;
  wherein said second alkaline scrubbing solution is the same as said first alkaline scrubbing solution and wherein said second acidic scrubbing solution is the same as said first acidic scrubbing solution.

17. A method for reducing the concentration of at least one odorous compound in a gas stream, comprising:
  passing a gas stream comprising at least one odorous compound through a first gas/liquid contactor;
  contacting said gas stream in said first gas/liquid contactor with an acidic liquid scrubbing solution;
  passing said gas stream from said first gas/liquid contactor through a second gas/liquid contactor; and
  contacting said gas stream in said second gas/liquid contactor with an alkaline liquid scrubbing solution comprising hydrogen peroxide without a hydrogen peroxide decomposition additive in said second gas/liquid contactor, wherein after a period of time said contacting in said first gas/liquid contactor is performed using said alkaline scrubbing solution instead of said acidic scrubbing solution and said contacting in said second gas/liquid contactor is performed using said acidic scrubbing solution instead of said alkaline scrubbing solution.

18. A method for reducing the concentration of at least one odorous compound in a gas stream, comprising:
  passing a gas stream comprising at least one odorous compound through a first gas/liquid contactor;
  contacting said gas stream in said first gas/liquid contactor with an alkaline liquid scrubbing solution comprising hydrogen peroxide without a hydrogen peroxide decomposition additive;
  passing said gas stream from said first gas/liquid contactor through a second gas/liquid contactor; and
  contacting said gas stream in said second gas/liquid contactor with an acidic liquid scrubbing solution in said second gas/liquid contactor, wherein after a period of time said contacting in said first gas/liquid contactor is performed using said acidic scrubbing solution instead of said alkaline scrubbing solution and said contacting in said second gas/liquid contactor is performed using said alkaline scrubbing solution instead of said acidic scrubbing solution.

* * * * *